US012731256B2

(12) United States Patent
Meguro

(10) Patent No.: US 12,731,256 B2
(45) Date of Patent: Sep. 8, 2026

(54) MEDICAL IMAGING APPARATUS AND OPERATION METHOD FOR MEDICAL IMAGING APPARATUS

(71) Applicant: FUJIFILM Corporation, Tokyo (JP)

(72) Inventor: Misaki Meguro, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 476 days.

(21) Appl. No.: 18/183,765

(22) Filed: Mar. 14, 2023

(65) Prior Publication Data

US 2023/0222663 A1 Jul. 13, 2023

Related U.S. Application Data

(63) Continuation of application No. PCT/JP2021/023936, filed on Jun. 24, 2021.

(30) Foreign Application Priority Data

Sep. 14, 2020 (JP) ................................ 2020-154181

(51) Int. Cl.
*G16H 30/40* (2018.01)
*A61B 1/00* (2006.01)
(Continued)

(52) U.S. Cl.
CPC ........ *G06T 7/0014* (2013.01); *A61B 1/00039* (2013.01); *A61B 1/0005* (2013.01);
(Continued)

(58) Field of Classification Search
CPC ......... G06T 7/0014; G06T 2207/10068; G06T 2207/30096; A61B 1/00039; A61B 1/0005; G16H 30/40; G16H 40/63
(Continued)

(56) References Cited

U.S. PATENT DOCUMENTS 8,370,293 B2 * 2/2013 Iwase ..................... G06F 16/00
707/608
9,262,444 B2 * 2/2016 Gross ................. G06F 3/04847
(Continued)

FOREIGN PATENT DOCUMENTS

CN 108122605 A * 6/2018
CN 110770842 A 2/2020
(Continued)

OTHER PUBLICATIONS

An Office Action mailed by the Japanese Patent Office on Mar. 26, 2024, which corresponds to Japanese Patent Application No. 2022-547408 and is related to U.S. Appl. No. 18/183,765.
(Continued)

*Primary Examiner* — Xiao Liu
*Assistant Examiner* — Eric James Shoemaker
(74) *Attorney, Agent, or Firm* — Studebaker Brackett PLLC

(57) ABSTRACT

At the time of automatic selection of a key image from among a large number of medical examination images, a medical imaging apparatus compares information extracted based on a sample image created in advance with information of an examination image, and performs common category determination and similarity degree determination. As a result of the comparison, the examination image selected to be close to the sample image is set as the key image, and storage processing is performed. The stored key image can be used for medical reports.

11 Claims, 9 Drawing Sheets

(51) Int. Cl.
*G06T 7/00* (2017.01)
*G16H 40/63* (2018.01)

(52) U.S. Cl.
CPC ............. *G16H 30/40* (2018.01); *G16H 40/63* (2018.01); *G06T 2207/10068* (2013.01); *G06T 2207/30096* (2013.01)

(58) Field of Classification Search
USPC .......................................................... 382/128
See application file for complete search history.

(56) References Cited

U.S. PATENT DOCUMENTS

2005/0251013 A1* 11/2005 Krishnan .............. G06T 7/0012 600/407
2008/0208791 A1 8/2008 Das et al.
2018/0293772 A1 10/2018 Akahori et al.
2018/0301216 A1* 10/2018 Nakamura ............. G16H 30/40
2019/0180863 A1* 6/2019 Reicher .................. G16H 30/40
2020/0126655 A1 4/2020 Sasaki et al.

FOREIGN PATENT DOCUMENTS

JP 2010-082277 A 4/2010
JP 2010-519659 A 6/2010
JP 2015-162082 A 9/2015
JP 2015-191561 A 11/2015
JP 2017-099509 A 6/2017
JP 2018175864 A * 11/2018 ........... A61B 5/7425
WO WO-2014080314 A1 * 5/2014 ............. G06T 11/60

OTHER PUBLICATIONS

International Search Report issued in PCT/JP2021/023936; mailed Sep. 28, 2021.
International Preliminary Report On Patentability (Chapter I) and Written Opinion of the International Searching Authority issued in PCT/JP2021/023936; issued Mar. 7, 2023.
An Office Action; mailed by the China National Intellectual Property Administration of the People's Republic of China on Mar. 7, 2026, which corresponds to Chinese Patent Application No. 202180063069.7 and is related to U.S. Appl. No. 18/183,765.

* cited by examiner 44
44a
· LESION: INFLAMMATION
· SITE: ESOPHAGOGASTRIC JUNCTION
· LIGHT SOURCE: WHITE LIGHT
· BIOPSY: NO
RETAIN/
EXTRACT
44b
· BRIGHTNESS
· NOISE
· RANGE
· ANGLE
31

SAMPLE IMAGE
53
21
54 55
SITE 1
LESION X
LESION Y
SITE 1
LESION Y
SITE 1
LIGHT SOURCE B
BIOPSY
SITE 2
LESION X
SITE 3
DELETE
21a
71
EDIT
ADD
57
59
58
52
59a

SAMPLE IMAGE
60
45
45a
SITE 1
LESION X
SITE 1
LESION Y
54
SITE 1
LIGHT SOURCE B
SITE 1
TREATMENT
SITE 2
LESION X
SITE 2
LESION Y
SITE 3
FINDINGS
STORE
72
DELETE
EXAMINATION IMAGE
SAMPLE IMAGE: PRESENT
ADD
46
46a
54
SITE 1
LESION X
SITE 1
LESION Y
71
SITE 3
RESELECT
73
57
61
52
SITE 2
LESION X
SITE 1
TREATMENT
SITE 2
LESION Y
TREATMENT

KEY IMAGE
SITE 1 LESION X
SITE 1 LESION Y
SITE 1 LIGHT SOURCE B
SITE 1 TREATMENT
SITE 2 LESION X
SITE 2 LESION Y
SITE 3
FINDINGS
STORE
EXAMINATION IMAGE
SAMPLE IMAGE: ABSENT
ADD
SITE 1 LESION X
SITE 1 LESION Y
SITE 3
SITE 1 LESION X
SITE 2 LESION X
SITE 1 TREATMENT
SITE 1 LESION Y
SITE 2 LESION Y
TREATMENT
RESELECT
31
31a
52
54
57
60
61
62
71
72
73

MEDICAL IMAGING APPARATUS AND OPERATION METHOD FOR MEDICAL IMAGING APPARATUS

CROSS-REFERENCE TO RELATED APPLICATIONS

This application is a Continuation of PCT International Application No. PCT/JP2021/023936 filed on 24 Jun. 2021, which claims priority under 35 U.S.C § 119(a) to Japanese Patent Application No. 2020-154181 filed on 14 Sep. 2020. The above application is hereby expressly incorporated by reference, in its entirety, into the present application.

BACKGROUND OF THE INVENTION

1. Field of the Invention

The present invention relates to a medical imaging apparatus for obtaining an image useful as a key image for use in creating a report and to an operation method for the medical imaging apparatus.

2. Description of the Related Art

In the medical field, a doctor diagnoses a patient while operating a device during an endoscope or ultrasound examination. After diagnosis, a key image including a region of interest or the like to be included in a report is selected from among acquired examination images, and is stored for creating a report. Since the standard or rule of the key image to be included in the report varies depending on the facility or doctor, the doctor himself/herself selects the key image from a large number of examination images captured at the time of diagnosis.

It takes time and effort to check the acquired examination images one by one and specify the key image including a region of interest such as a lesion, which is a burden on the doctor. Therefore, a technique for supporting easy acquisition of the key image is being developed.

In JP2017-99509A, a sample image is displayed at the time of endoscope imaging, and a user refers to the sample image to easily capture an image including a region of interest and to acquire an image useful as a key image.

SUMMARY OF THE INVENTION

Even if a useful image is acquired at the time of imaging, it is necessary to find it from among a large number of medical examination images to select a key image.

An object of the present invention is to provide a medical imaging apparatus that allows a user to select a key image from among a large number of medical examination images without a burden and to provide an operation method for the medical imaging apparatus.

A medical imaging apparatus according to the present invention includes a processor, the processor being configured to: acquire sample images created in advance and obtained by imaging an inside of a body; compare examination image information attached to examination images obtained by imaging an inside of a body with sample image information attached to the sample images to select a key image from among the examination images; and display the selected key image on a screen.

The processor is preferably configured to: extract the sample image information from the sample images; and extract the examination image information from the examination images.

The processor is preferably configured to: compare examination image category information included in the examination image information with sample image category information included in the sample image information; and determine a common category to select the key image.

The processor is preferably configured to: compare examination image quality information included in the examination image information with sample image quality information included in the sample image information; and determine a degree of similarity to select the key image.

The processor is preferably configured to display a list of the sample images and the sample image information attached to the sample images, the sample images and the sample image information being used to select the key image.

The processor is preferably configured to receive a user input for adding or deleting any of the sample images and editing the sample image information attached to the sample images.

The processor is preferably configured to display, on the screen, the selected key image and a non-selected examination image together with the examination image information attached to the selected key image and the non-selected examination image.

The processor is preferably configured to display, on the screen, that the selected key image is related to the sample image information.

The processor is preferably configured to display, on the screen, that the sample images are absent if the sample images are absent.

The processor is preferably configured to receive the user input for adding, to the key image, the non-selected examination image displayed on the screen.

The sample image information and the examination image information preferably have at least one of information on an image quality of an image, information on a lesion, information on an imaging site, information on a biopsy, information on treatment, information on a light source, or information on device settings.

The sample images are preferably previous report images used in a previous report or user selection images selected by a user, and the processor is preferably configured to acquire the sample images from a database.

An operation method for a medical imaging apparatus, including a processor, the processor including: a step of acquiring sample images created in advance and obtained by imaging an inside of a body; a step of comparing examination image information of examination images obtained by imaging an inside of a body with sample image information of the sample images to select a key image from among the examination images; and a step of displaying the selected key image on a screen.

According to the present invention, a user can select a key image from among a large number of medical examination images without a burden.

DESCRIPTION OF THE PREFERRED EMBODIMENTS

First Embodiment

Figure 1:
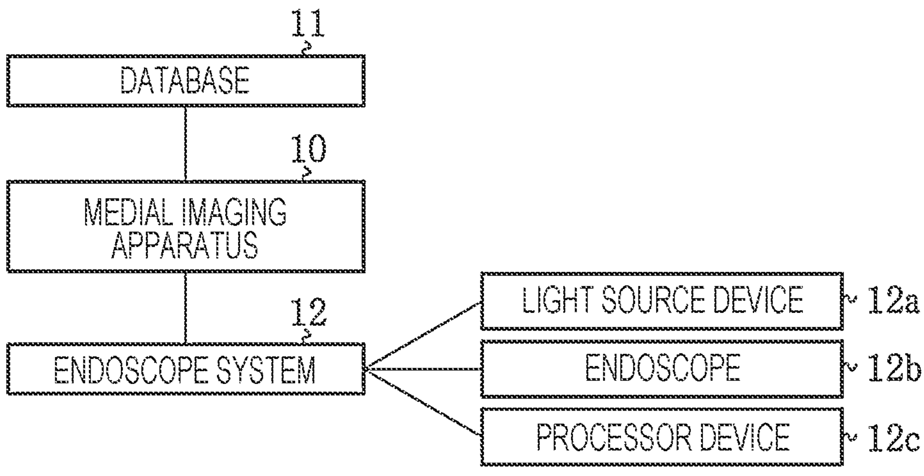
FIG. 1 is a schematic diagram illustrating a medical imaging apparatus, a database, and an endoscope system, the database and the endoscope system being connected to the medical imaging apparatus.

As illustrated in FIG. 1, a medical imaging apparatus 10 is connected to a database 11 and an endoscope system 12. The medical imaging apparatus 10 transmits sample images 21 created in advance by a user from the database 11 to a sample information acquisition unit 20. In addition, the endoscope system 12 includes a light source device 12*a*, an endoscope apparatus 12*b*, and a processor device 12*c*, and transmits examination images 31 acquired by imaging to an examination image acquisition unit 30.

In the medical imaging apparatus 10, programs relating to various processes are incorporated in a program memory (not illustrated). The medical imaging apparatus 10 is provided with a central control unit (not illustrated) configured by a processor. The central control unit executes the programs in the program memory to implement the functions of the sample information acquisition unit 20, the examination image acquisition unit 30, a key image selection unit 40, a common category determination unit 41, a similarity degree determination unit 42, an image display unit 50, a display control unit 51, an input reception unit 70, a key image storage memory 80, and a report creation device 90.

Figure 2:
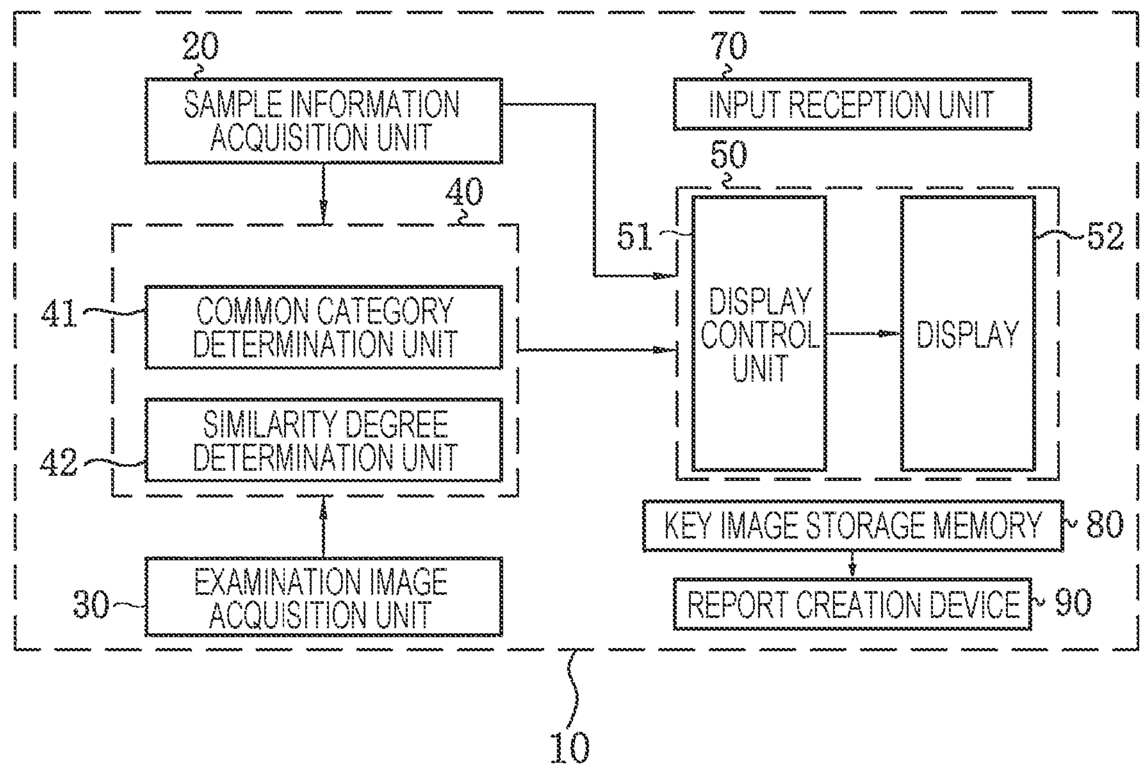
FIG. 2 is a block diagram illustrating functions of the medical imaging apparatus.

As illustrated in FIG. 2, the medical imaging apparatus 10 has the sample information acquisition unit 20, the examination image acquisition unit 30, the key image selection unit 40, the image display unit 50, the input reception unit 70, the key image storage memory 80, and the report creation device 90. The key image selection unit 40 includes the common category determination unit 41 and the similarity degree determination unit 42, and the image display unit 50 has the display control unit 51 and a display 52.

The sample information acquisition unit 20 retains the sample images 21 acquired from the database 11 and extracts sample image information 43 from each of the sample images 21. Extraction of the sample image information 43 is performed by machine learning, image processing, image analysis, or the like. The extracted sample image information 43 has sample image category information 43*a* and sample image quality information 43*b*, is attached to the sample image 21 that is the extraction source, and is transmitted to the key image selection unit 40 at the time of automatic selection of a key image 45. The sample image 21 is an image serving as a sample of the key image 45 used at the time of report creation.

The examination image acquisition unit 30 stores the examination images 31 acquired from the endoscope system 12 and examination image information 44 attached to the examination images 31. In addition, the examination image information 44 is extracted by machine learning, image processing, image analysis, or the like in a form of being added to the examination image information 44 acquired at the time of imaging. The extracted examination image information 44 has examination image category information 44*a* and examination image quality information 44*b*, is attached to the examination image 31 that is the extraction source, and is transmitted to the key image selection unit 40 at the time of automatic selection of the key image 45.

In the key image selection unit 40, the common category determination unit 41 compares the sample image category information 43*a* with the examination image category information 44*a* to determine common category information, and the similarity degree determination unit 42 compares the sample image quality information 43*b* with the examination image quality information 44*b* to determine the degree of similarity such as numerical values of the image quality information. For the key image selection from among the examination images 31, automatic selection is performed by combining both results obtained by the common category determination unit 41 and the similarity degree determination unit 42. The order of performing the common category determination and the similarity degree determination may be reversed.

In the image display unit 50, the display control unit 51 receives key images 45 transmitted from the key image selection unit 40 and non-selected examination images 46 that are not selected as the key images 45, and causes the display 52 to display the key images 45 and the non-selected examination images 46 together with respective pieces of the examination image category information 44*a* in a superimposed manner.

The input reception unit 70 receives inputs such as editing of the sample image information 43 and the examination image information 44, an operation of setting at the time of automatic selection of the key images 45, and selection of an image via a user interface such as a keyboard or a mouse.

The key image storage memory 80 stores both the examination images 31 selected as the key images 45 and the examination image information 44 attached to the examination images 31, and outputs them to the report creation device 90 at the time of report creation.

Figures 3, 4:
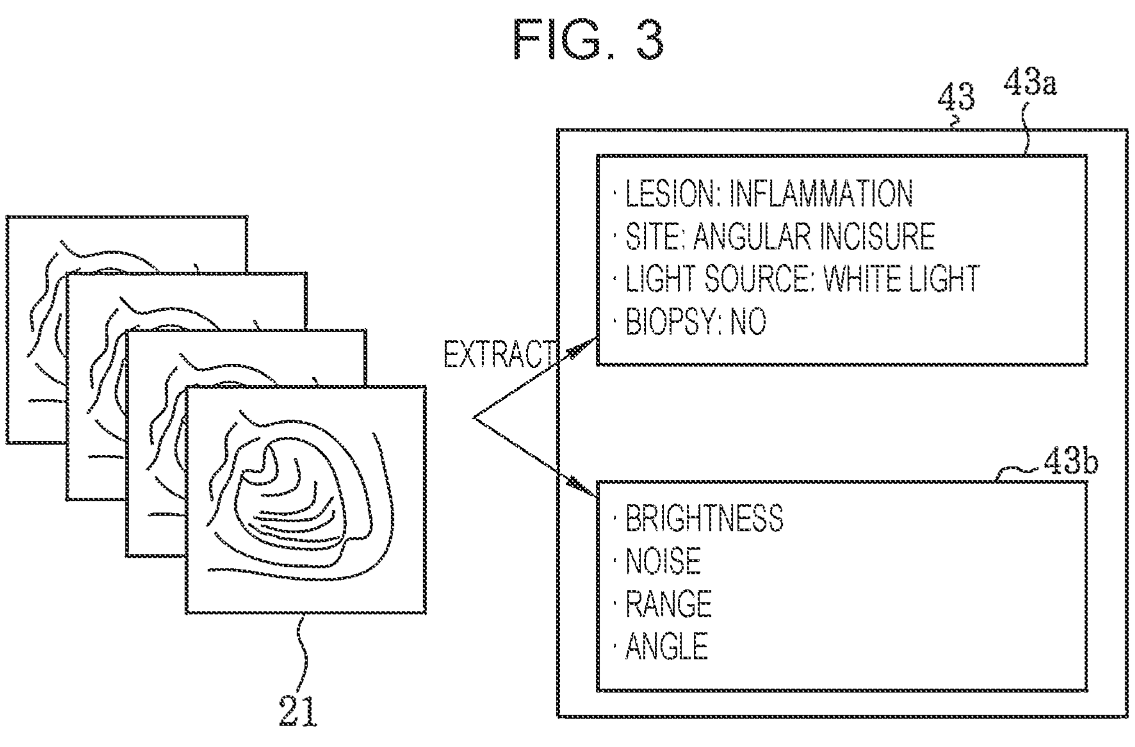
FIG. 3 is an explanatory diagram illustrating extraction of sample image category information from sample images.
FIG. 4 is an explanatory diagram illustrating extraction of examination image category information from examination images.

As illustrated in FIG. 3, the sample information acquisition unit 20 extracts the sample image information 43 from each of the sample images 21 by using machine learning, image processing, image analysis, or the like. The sample image information 43 has the sample image category information 43*a*, which is category information, including at least one of a lesion in the image, a site, a biopsy, treatment, a light source, or device settings, and the sample image quality information 43*b*, which is numerical value information, including at least one of a brightness of the image, a noise, an imaging distance, or an imaging angle. The extracted sample image information 43 is attached to the sample image 21 that is the source. If it is not possible to extract a piece of information, the piece of information can be added to the sample image 21 by user input.

As illustrated in FIG. 4, the examination image acquisition unit 30 extracts the examination image information 44 from each of the examination images 31 by using machine learning, image processing, image analysis, or the like, as in the sample images 21. The examination image information 44 has the examination image category information 44*a*, which is category information, including at least one of a lesion in the image, a site, a biopsy, treatment, a light source, or device settings, and the examination image quality information 44*b*, which is numerical value information, including at least one of a brightness of the image, a noise, an imaging distance, or an imaging angle. The examination image information 44 acquired at the time of endoscopic imaging is held as it is, and the examination image information 44 extracted in the form of being added is attached to the examination image 31 that is the source. If it is not possible to acquire a piece of information, the piece of information can be added to the examination image 31 by user input.

Figure 5:
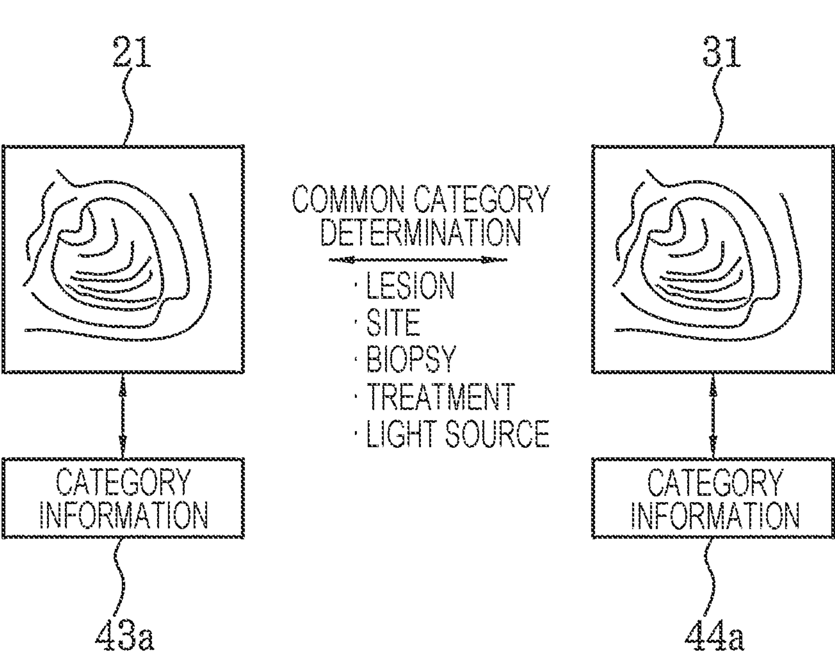
FIG. 5 is an explanatory diagram for determining a common category by comparing a sample image with an examination image.

As illustrated in FIG. 5, each of the plurality of sample images 21 and each of the plurality of examination images 31 transmitted to the key image selection unit 40 are subjected to determination by the common category determination unit 41 as to whether the sample image category information 43*a* of the sample image 21 and the examination image category information 44*a* of the examination image 31 have a common category by comparison processing. As a result of the comparison processing, an examination image 31 with a certain number or more of pieces of the examination image category information 44*a* common to the sample image category information 43*a* of any of the sample images 21 is selected. The certain number is a threshold value of the number of one or more common categories that can be freely set by a user. After the common category determination, the examination image 31 is transmitted to the similarity degree determination unit 42.

As a specific example, if there is a sample image 21 having the sample image category information 43*a* of "lesion=inflammation", "site=angular incisure", "light source=white light", "treatment=no", and "biopsy=no", and if the threshold value of the number of common categories between the sample image category information 43*a* and the examination image category information 44*a* is set to "3", an examination image 31 having the examination image category information 44*a* common to at least three pieces of the above category information is selected in the common category determination by comparison processing.

Figure 6:
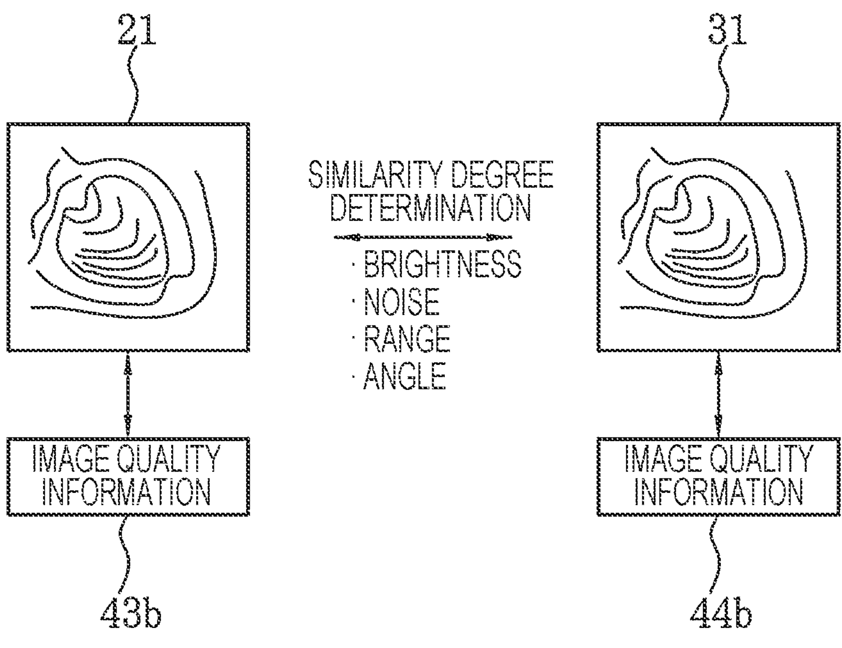
FIG. 6 is an explanatory diagram for determining a degree of similarity by comparing a sample image with an examination image.

As illustrated in FIG. 6, each of the sample images 21 and each of the examination images 31 transmitted from the common category determination unit 41 are subjected to determination by the similarity degree determination unit 42 as to how much the numerical values of the respective items of the examination image quality information 44*b* of the examination image 31 are similar to the numerical values of the respective items of the sample image quality information 43*b* of the sample image 21 by comparison processing. As a result of the similarity degree determination, an examination image 31 having a degree of similarity greater than or equal to a certain value with respect to any of the sample images 21 is selected. Here, the certain value is a threshold value of the degree of similarity that can be freely set by a user. The degree of similarity may be expressed as a percentage, or may be classified into five or ten levels. Examination images 31 selected as having the examination image information 44 greater than or equal to the threshold values of both the common category determination and the similarity degree determination are transmitted to the display control unit 51 as the key images 45, and the other examination images 31 are transmitted to the display control unit 51 as the non-selected examination images 46.

As a specific example, if the comparison processing is performed on the degree of similarity between "brightness", "noise", "imaging range", and "imaging angle" of the sample image quality information 43*b* of a sample image 21 and the respective items of the examination image quality information 44*b*, a matching rate with each item of the sample image quality information 43*b* can be calculated, and the overall evaluation of the matching rates for the respective items can be evaluated as the degree of similarity. The number of items to be compared is preferably three or more. The higher the degree of similarity, the larger the number of items that can be compared, and the higher the matching rate for each item.

In the comparison processing illustrated in FIGS. 5 and 6, the key images 45 are selected by setting each threshold value, but in addition thereto, the examination images 31 to be selected as the key images 45 may be further narrowed down. For example, a given number of the examination images 31 are selected as the key images 45 in descending order of the number of common categories or in descending order of the degree of similarity from among the examination images 31 narrowed down by the common category determination and the similarity degree determination.

Figure 7:
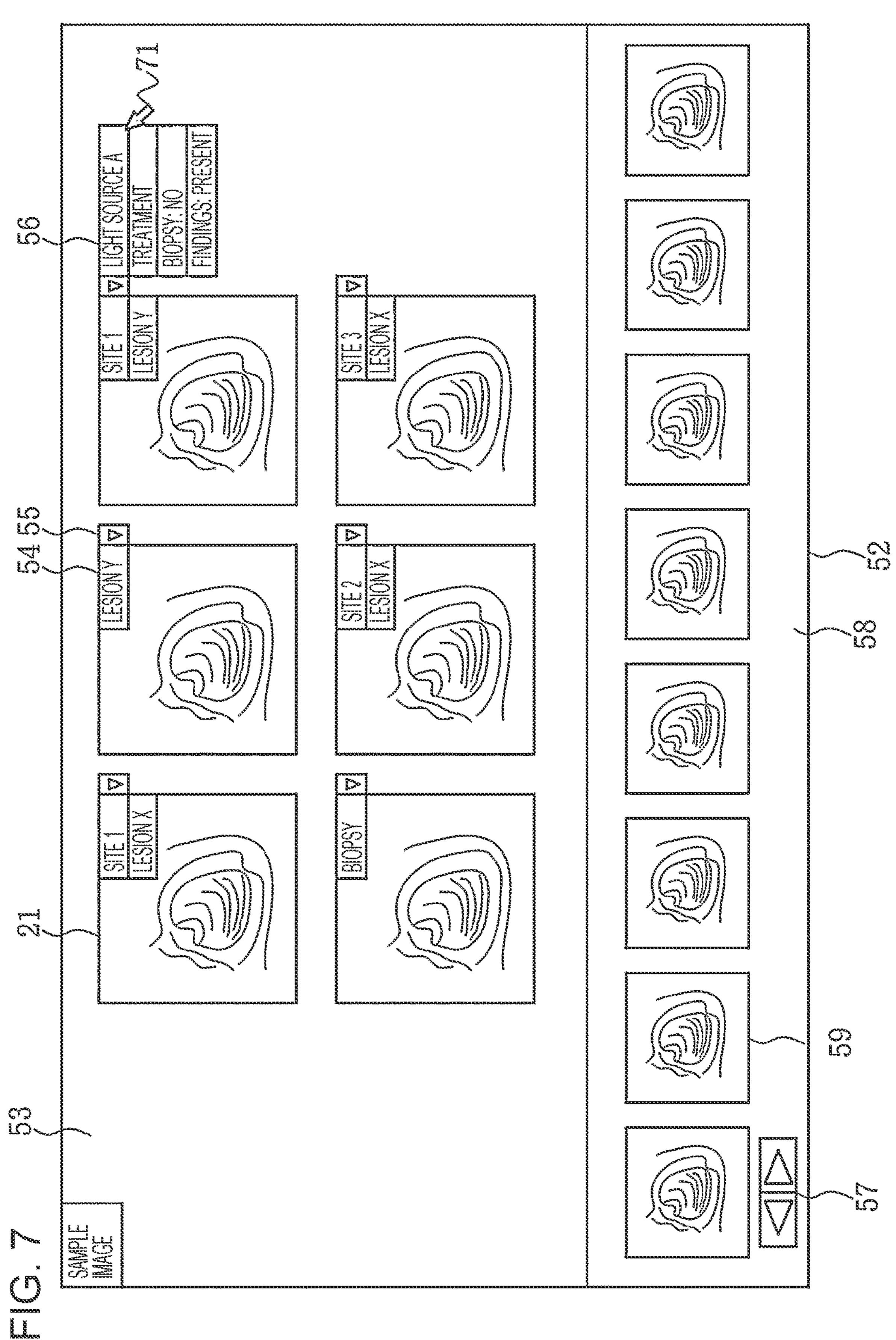
FIG. 7 is an image diagram illustrating a list of sample images displayed such that category information is superimposed thereon.

As illustrated in FIG. 7, a list of the sample images 21 is displayed on the display 52. A user can check the sample images 21 that are created in advance and displayed in a sample image display field 53 of the display 52. The sample information acquisition unit 20 extracts the sample image category information 43*a* from each of the sample images 21 and attaches it to the sample images 21 that is the source. The list of the sample images 21 is displayed via the display control unit 51. A category information display field 54 is provided for each of the sample images 21 displayed in a list, and the attached sample image category information 43*a* can be displayed in a superimposed manner. The number of pieces of the sample image category information 43*a* to be displayed in a superimposed manner is preferably about one or two. In addition, one piece of the sample image category information 43*a* to be displayed in a superimposed manner is preferably a lesion or an imaged site. Furthermore, a database image display field 58, which is displayed simultaneously with the sample image display field 53, can be provided to display a list of database images 59 stored in the database 11.

In addition, as illustrated in FIG. 7, the superimposed display content of the sample image category information 43*a* of the sample images 21 is switchable. In response to a user selecting a pull-down menu display button 55 of the category information display field 54 with a cursor 71 via the input reception unit 70 by a mouse operation or the like, other pieces of the sample image category information 43*a*, such as light source, biopsy, image quality, and device settings, which have been hidden, are displayed in a pull-down menu 56. A desired item of the sample image category information 43*a* can be selected with the cursor 71 from the pull-down menu 56 and can be switched.

Figure 8:
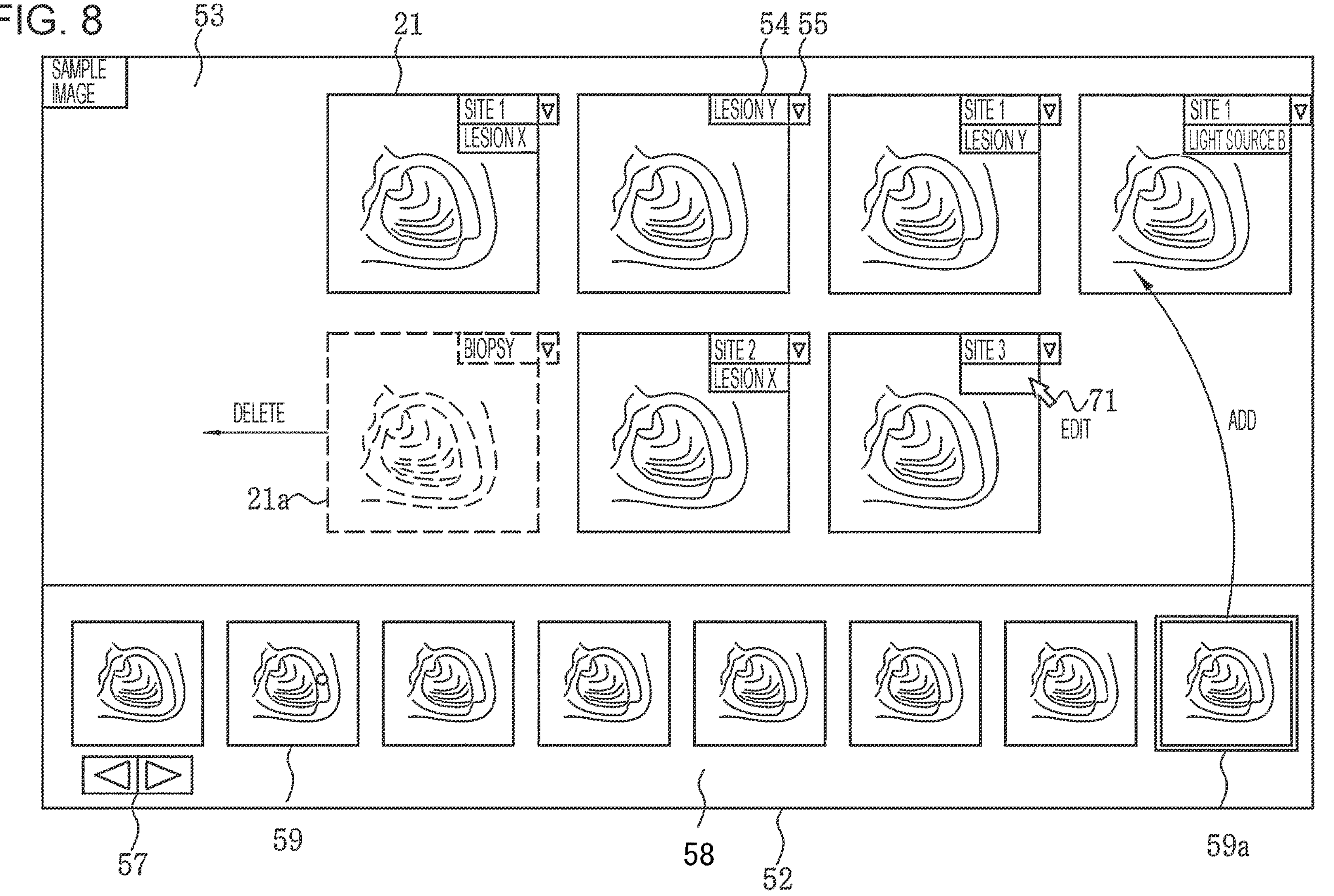
FIG. 8 is an image diagram illustrating editing of a given sample image by user input.

As illustrated in FIG. 8, a user can add or delete any of the sample images 21 and edit the sample image category information 43*a* through input by a mouse operation or the like. The user can delete a selected sample image 21*a* from among the sample images 21 displayed in a list in the sample image display field 53 of the display 52, add a selected database image 59*a* to the sample images 21 from among the database images 59 displayed in a list in the database image display field 58, and edit the sample image category information 43*a* in any of the category information display fields 54 superimposed on the sample images 21 by user input using keyboard input or the like, such as changing or correcting information. The sample image 21 and the sample image category information 43*a* for user input is selected with the cursor 71 by a mouse operation or the like. In the case of referring to the database images 59 other than the images displayed in the database image display field 58, the database images 59 to be displayed in a list can be switched by using a page switching button 57. After the user input is completed, the sample images 21 and the sample image category information 43*a* that are stored are transmitted to the key image selection unit 40, and are subjected to the comparison processing with the examination images 31.

Figure 9:
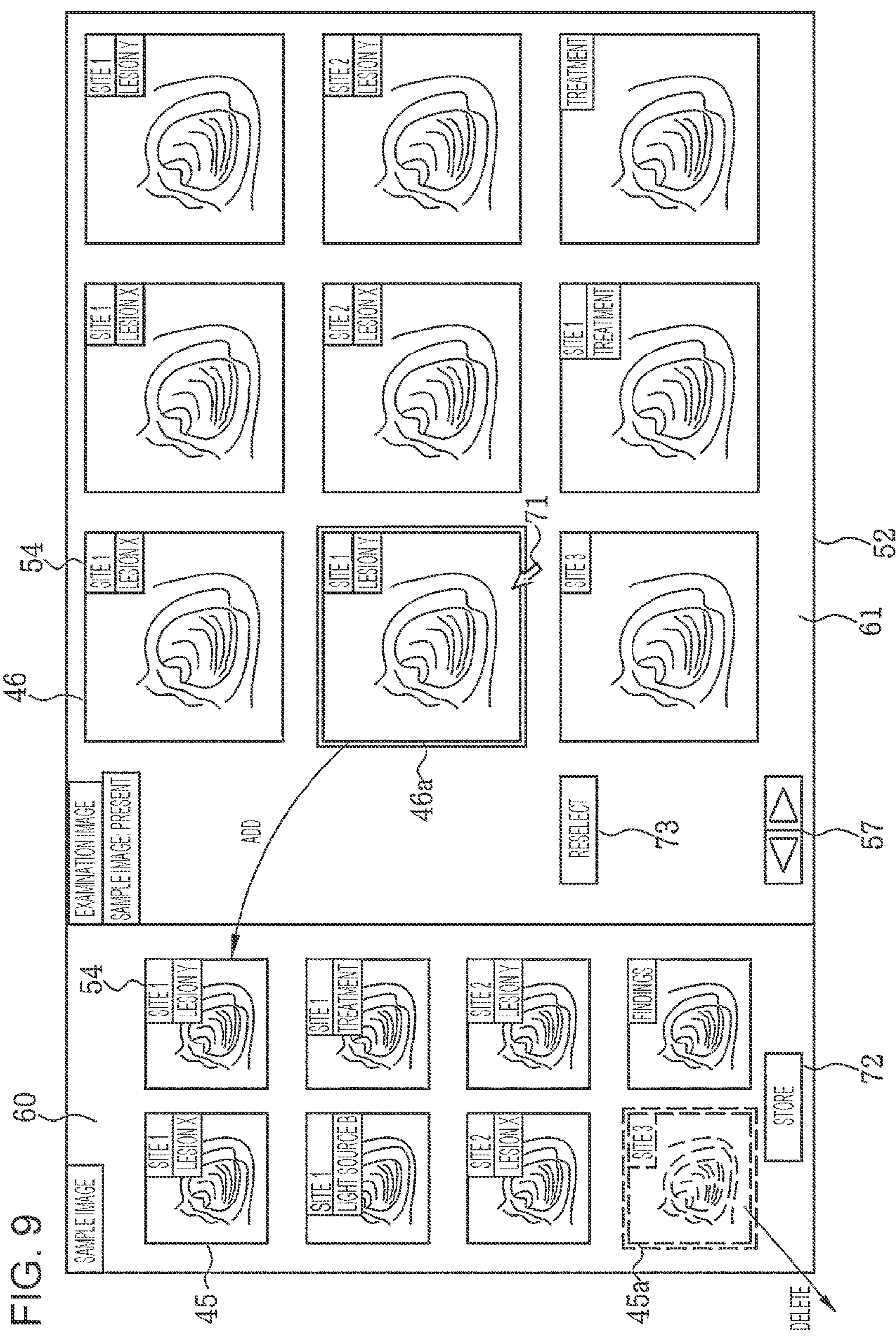
FIG. 9 is an image diagram in which a selected key image and a non-selected examination image are displayed on a screen.

As illustrated in FIG. 9, the result of automatic selection of the key images 45 can be displayed on the display 52. A list of the selected key images 45 is displayed in a key image display field 60, and a list of the non-selected examination images 46 is displayed in an examination image display field 61. In the key images 45 and the non-selected examination images 46, the examination image category information 44*a* common to the sample image 21 is displayed in a superimposed manner in the category information display field 54 on each image.

A non-selected examination image 46 displayed on the display 52 can be added to the key images 45 by user input. In addition, a given key image 45*a* displayed on the display 52 can be deleted from the key images 45 by user input.

A user checks the key images 45 displayed in the key image display field 60 of the display 52, and if there is no problem, selects a store button 72 to store the key images 45. The key images 45 are stored in the key image storage memory 80.

Figure 10:
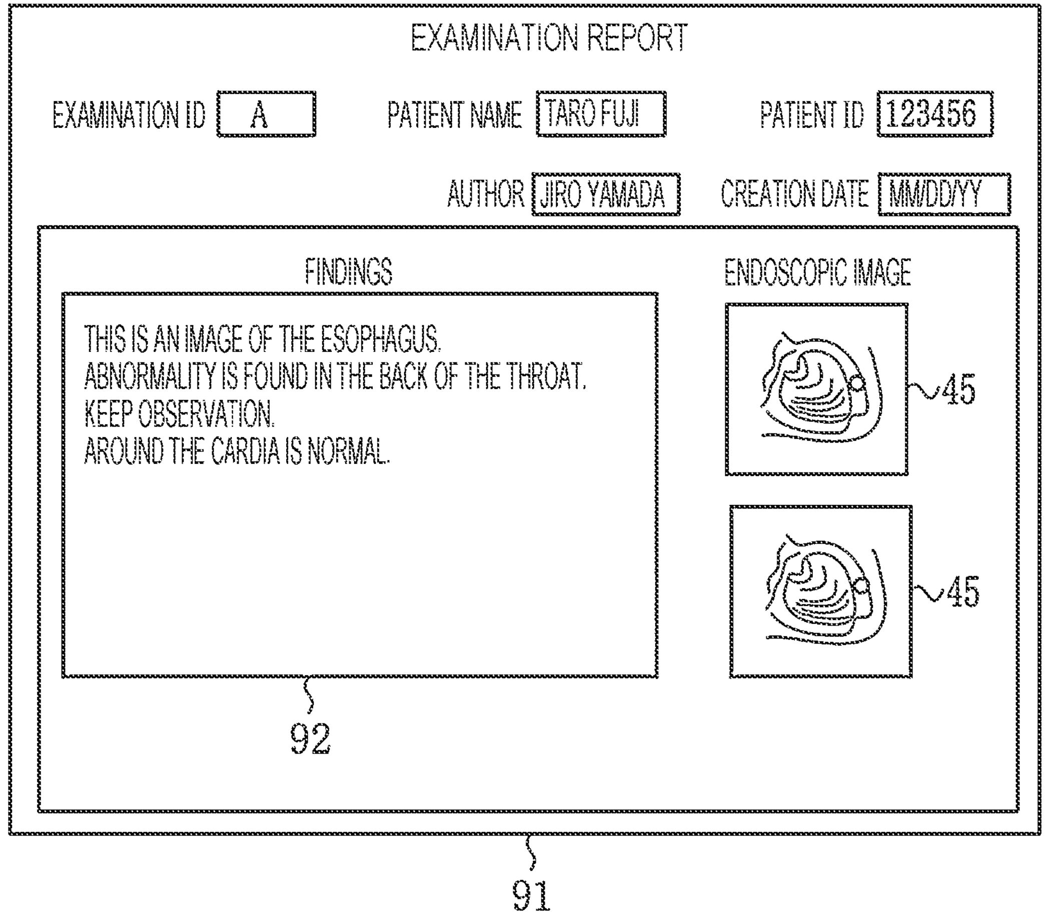
FIG. 10 is an image diagram illustrating report creation using selected key images.

As illustrated in FIG. 10, the key images 45 stored in the key image storage memory 80 are transmitted to the report creation device 90 and used to create a report 91. In the creation of the report 91, a doctor's findings are input to a findings input field 92, and the key images 45 corresponding to the contents of the findings are pasted.

It is possible to check the key images 45 displayed in the key image display field 60 of the display 52, and to reselect the key images 45 if the quality, quantity, or type is insufficient, for example. If the re-selection is performed, a reselection button 73 on the examination image display field 61 of the display 52 is selected by a cursor, and the result of the key image selection is reset.

It is preferable that the reset of the selection result is performed only for the selection result of the examination images 31 by the comparison processing in the key image selection unit 40, and the results of the extraction, the attachment, and the user input of each piece of image information are left.

If the reselection is performed, at least one operation of editing one or both of the sample image information 43 and the examination image information 44, adding or deleting any of the sample images 21, changing the setting of the key image selection unit 40, or the like is performed by user input to change the conditions of the key image selection.

Second Embodiment

A second embodiment relates to selection of the key images 45 in a case where no sample images 21 are acquired. In the second embodiment, the content common to the first embodiment will be omitted.

The key image selection unit 40 performs comparison processing with category information input by a user instead of the sample image category information 43*a*. The category information freely set by the user is compared with the examination image category information 44*a* to perform the common category determination. The examination images 31 after the determination are transmitted to the display control unit 51.

Figure 11:
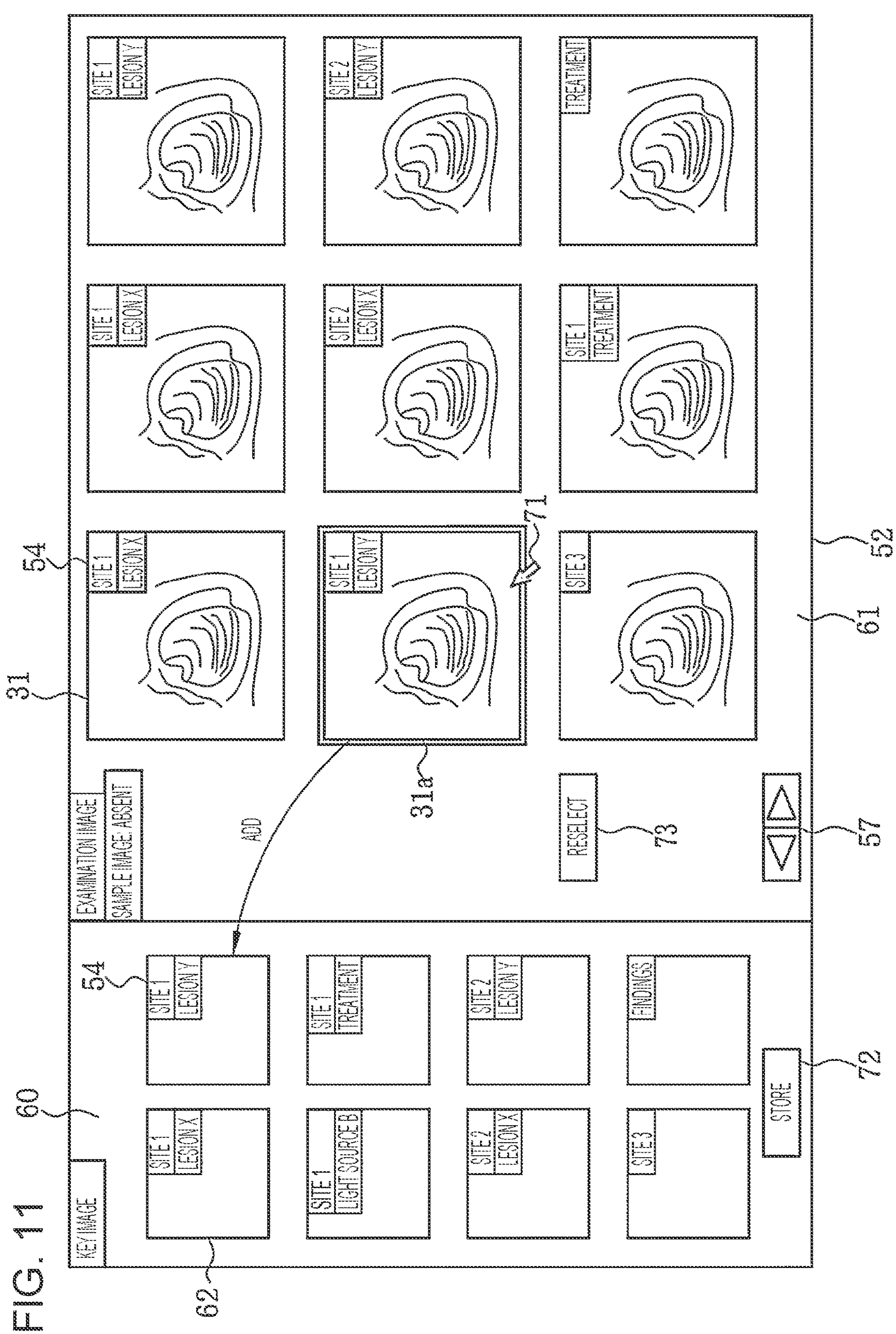
FIG. 11 is an image diagram of a screen on which a key image is manually selected without using sample images.

As illustrated in FIG. 11, in the present embodiment, the examination images 31 subjected to the common category determination by the key image selection unit 40 and transmitted to the display control unit 51 are not automatically displayed in the key image display field 60 of the display 52, but are displayed in a list in the examination image display field 61. Key image display frames 62 are displayed at positions where the key images 45 are displayed in the first embodiment in the key image display field 60, and the category information display fields 54 are displayed. The key image display frames 62 are frames for displaying manually selected examination images 31 as the key images 45. In the category information display fields 54 on the examination images 31, respective pieces of the examination image category information 44*a* common to the category information set by the user are displayed. Examination images 31 less than the threshold value in the common category determination result in the key image selection unit 40 are not displayed in the examination image display field 61.

The user manually selects an examination image 31*a* to be added to the key images 45 from among the examination images 31 displayed in the examination image display field 61 with the cursor 71 by a mouse operation or the like. The examination image 31*a* that is manually selected is displayed in a key image display frame 62 with common category information in the key image display field 60 by user input. In addition, a message indicating that no sample images 21 are used is displayed on the display 52.

Upon obtaining a sufficient number of key images 45 by manual addition, the user selects the store button 72 with the cursor 71 and stores the key images 45 in the key image storage memory 80.

Figure 12:
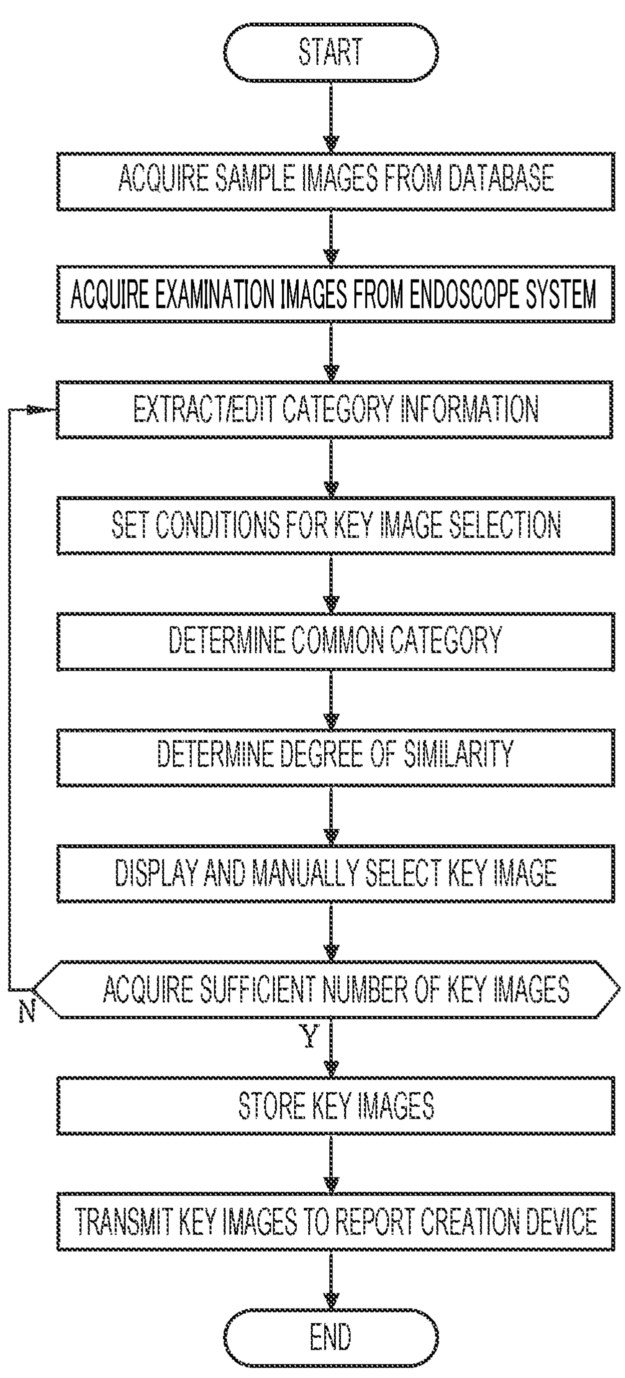
FIG. 12 is a flowchart illustrating a sequential flow of the present invention.

A sequential flow of automatic selection of key images 45 will be described with reference to a flowchart illustrated in FIG. 12. First, the sample images 21 created in advance are acquired from the database 11 connected to the medical imaging apparatus 10 and are stored in the sample information acquisition unit 20. In addition, the examination images 31 captured by the endoscope system 12 are stored in the examination image acquisition unit 30.

After the sample images 21 are acquired, the sample image information 43 is extracted from each of the sample images 21 stored in the sample information acquisition unit 20 by using machine learning or the like. The extracted sample image information 43 having the sample image category information 43*a* and the sample image quality information 43*b* is attached to the sample image 21 that is the source.

At this time, by displaying a list of the sample images 21 on the display 52, it is possible to check the sample images 21 and perform user input of the sample image information 43. After the user input, the sample images 21 and the sample image information 43 attached to the sample images 21 are transmitted to the key image selection unit 40.

For each of the examination images 31, as in the sample images 21, in a form of being added to information that is acquired at the time of imaging by the endoscope system 12 and attached, information can be extracted and attached to the examination image 31 that is the source. Note that only the examination image information 44 acquired at the time of imaging may be attached to the examination images 31 without extracting information. The examination images 31 to which the examination image information 44 is attached are transmitted to the key image selection unit 40.

Before starting automatic selection of key images 45, a user sets conditions for the key image selection. The user can adjust the number of images to be selected as the key images 45 by setting threshold values of the number of pieces of common category information and the degree of similarity. Previously set conditions may be repeatedly used as the selection conditions.

The sample images 21, the examination images 31, and respective pieces of image information are transmitted to the key image selection unit 40, and key image selection is performed. In the key image selection unit 40, the common category determination unit 41 and the similarity degree determination unit 42 perform comparison processing. Either the common category determination or the similarity degree determination may be performed first.

The common category determination unit 41 performs comparison processing between the sample image category information 43*a* and the examination image category information 44*a*. It can be determined that, as the number of pieces of the examination image category information 44*a* common to the sample image category information 43*a* of any of the sample images 21 is larger, the examination image 31 that is the source is closer to the sample image 21.

The similarity degree determination unit 42 performs comparison processing between numerical values of the sample image quality information 43*b* and the examination image quality information 44*b*, and determines the degree of similarity. It can be determined that, as the degree of similarity of the examination image quality information 44*b* is higher with respect to the sample image quality information 43*b* of any of the sample images 21, the examination image 31 that is the source is more similar to the sample image 21.

By combining the comparison processing results obtained by the common category determination unit 41 and the similarity degree determination unit 42, the examination image 31 close to any of the sample images 21 is selected as the key image 45. The selection of the key images 45 is a result of the common category determination and the similarity degree determination on the sample images 21 and the examination images 31 of the same combination. The examination images 31 selected as the key images 45 are transmitted to the image display unit 50 together with the non-selected examination images 46.

The key images 45 and the non-selected examination images 46 transmitted to the image display unit 50 are displayed in a list on the display 52 via the display control unit 51. The sufficient number of selected key images 45 are checked, and if there is no problem, storage processing is performed. A non-selected examination image 46 displayed by user input can be added to the key images 45. Reselection can also be performed.

If reselection is performed, each piece of image information is edited, and the threshold value in the common category determination or the similarity degree determination is changed, for example. If there is a key image 45 to be stored before the reselection, the key image 45 may be stored.

The key images 45 subjected to the storage processing is stored in the key image storage memory 80 and output to the report creation device 90. The report 91 is created in the report creation device.

In the above embodiments, a hardware configuration of processing units that perform various kinds of processing, such as the sample information acquisition unit 20, the examination image acquisition unit 30, the key image selection unit 40, the common category determination unit 41, the similarity degree determination unit 42, the image display unit 50, the display control unit 51, the input reception unit 70, the key image storage memory 80, and the report creation device 90, is any of the following various processors. Various processors include a CPU (Central Processing Unit), a GPU (Graphical Processing Unit), a PLD (Programmable Logic Device), a dedicated electric circuit, and the like. The CPU and the GPU are general-purpose processors that function as various processing units by executing software (programs). The PLD is a processor in which the circuit configuration is changeable after manufacture, such as FPGA (Field Programmable Gate Array). The dedicated electric circuit is a processor having a circuit configuration that is specially designed to execute various kinds of processing.

One processing unit may be configured by one of these various processors, or may be configured by a combination of two or more processors of the same type or different types (e.g., a combination of a plurality of FPGAs, a combination of a CPU and an FPGA, or a combination of a CPU and a GPU). In addition, a plurality of processing units may be configured as one processor. Firstly, as an example of configuring a plurality of processing units using one processor, there is a form in which one processor is configured by a combination of one or more CPUs and software, and the processor functions as a plurality of processing units. Secondly, there is a form using a processor that implements the functions of the entire system including a plurality of processing units by using one IC (Integrated Circuit) chip, as typified by a system on chip (SoC) or the like. In this manner, various processing units are configured by one or more of the above various processors in terms of hardware configuration.

More specifically, the hardware configuration of these various processors is electric circuitry configured by a combination of circuit elements such as semiconductor elements. The hardware configuration of the storage unit is a storage device such as an HDD (hard disc drive) or an SSD (solid state drive).

REFERENCE SIGNS LIST

10 medical imaging apparatus
11 database
12 endoscope system
12*a* light source device
12*b* endoscope
12*c* processor device
20 sample information acquisition unit
21 sample image
21*a* sample image
30 examination image acquisition unit
31 examination image
31*a* examination image
40 key image selection unit
41 common category information determination unit
42 similarity degree determination unit
43 sample image information
43*a* sample image category information
43*b* sample image quality information
44 examination image information
44*a* examination image category information

44*b* examination image quality information
45 key image
45*a* key image
46 non-selected examination image
46*a* non-selected examination image
50 image display unit
51 display control unit
52 display
53 sample image display field
54 category information display field
55 pull-down menu display button
56 pull-down menu
57 page switching button
58 database image display field
59 database image
59*a* database image
60 key image display field
61 examination image display field
62 key image display frame
70 input reception unit
71 cursor
72 store button
73 reselection button
80 key image storage memory
90 report creation device
91 report
92 findings input field

What is claimed is:

1. A medical imaging apparatus comprising a processor, the processor being configured to:

acquire sample images created in advance and obtained by imaging an inside of a body;

compare examination image information attached to examination images obtained by imaging an inside of a body with sample image information attached to the sample images to select a key image from among the examination images;

compare examination image category information included in the examination image information with sample image category information included in the sample image information, and compare examination image quality information included in the examination image information with sample image quality information included in the sample image information;

determine a common category between the examination image category information and the sample image category information, and a degree of similarity between the examination image quality information and the sample image quality information;

select the key image in descending order of the number of the common category or the descending order of the degree of similarity, wherein the examination image with the number of the common category equal to or greater than a threshold is selected as the key image; and display the selected key image on a screen.

2. The medical imaging apparatus according to claim 1, wherein the processor is configured to:

extract the sample image information from the sample images; and extract the examination image information from the examination images.

3. The medical imaging apparatus according to claim 1, wherein the processor is configured to display a list of the sample images and the sample image information attached to the sample images, the sample images and the sample image information being used to select the key image.

4. The medical imaging apparatus according to claim 1, wherein the processor is configured to receive a user input for adding or deleting any of the sample images and editing the sample image information attached to the sample images.

5. The medical imaging apparatus according to claim 1, wherein the processor is configured to display, on the screen, the selected key image and a non-selected examination image together with the examination image information attached to the selected key image and the non- selected examination image.

6. The medical imaging apparatus according to claim 1, wherein the processor is configured to display, on the screen, that the selected key image is related to the sample image information.

7. The medical imaging apparatus according to claim 1, wherein the processor is configured to display, on the screen, that the sample images are absent if the sample images are absent.

8. The medical imaging apparatus according to claim 1, wherein the processor is configured to receive user input selecting a non-selected examination image to be used as a key image.

9. The medical imaging apparatus according to claim 1, wherein the sample image information and the examination image information have at least one of information on an image quality of an image, information on a lesion, information on an imaging site, information on a biopsy, information on treatment, information on a light source, or information on device settings.

10. The medical imaging apparatus according to claim 1, wherein the sample images are previous report images used in a previous report or user selection images selected by a user, and the processor is configured to acquire the sample images from a database.

11. An operation method for a medical imaging apparatus, comprising:

a step of acquiring sample images created in advance and obtained by imaging an inside of a body;

a step of comparing examination image information of examination images obtained by imaging an inside of a body with sample image information of the sample images to select a key image from among the examination images;

a step of comparing examination image category information included in the examination image information with sample image category information included in the sample image information, and comparing examination image quality information included in the examination image information with sample image quality information included in the sample image information;

a step of determining a common category between the examination image category information and the sample image category information, and a degree of similarity between the examination image quality information and the sample image quality information;

a step of selecting the key image in descending order of the number of the common category or the descending order of the degree of similarity, wherein the examination image with the number of the common category equal to or greater than a threshold is selected as the key image; and a step of displaying the selected key image on a screen.

* * * * *